United States Patent
Lee et al.

(10) Patent No.: US 6,294,179 B1
(45) Date of Patent: Sep. 25, 2001

(54) METHOD OF EXFOLIATING SKIN

(75) Inventors: Robert Stanley Lee; David Serridge, both of Merseyside (GB)

(73) Assignee: Lever Brothers Company, Division of Conopco, Inc., New York, NY (US)

( * ) Notice: Subject to any disclaimer, the term of this patent is extended or adjusted under 35 U.S.C. 154(b) by 0 days.

(21) Appl. No.: 08/653,100

(22) Filed: May 24, 1996

Related U.S. Application Data

(62) Division of application No. 08/417,702, filed on Apr. 6, 1995, now abandoned, which is a continuation of application No. 08/065,330, filed on May 20, 1993, now abandoned.

(30) Foreign Application Priority Data

| May 21, 1992 | (GB) | 9210870 |
| Jun. 12, 1992 | (GB) | 9212579 |

(51) Int. Cl.[7] ............... A61K 7/00; A61K 7/50
(52) U.S. Cl. ............ 424/401; 510/109; 510/130; 510/139
(58) Field of Search ............... 424/401, 70.1; 510/109, 130, 139

(56) References Cited

U.S. PATENT DOCUMENTS

| 3,092,111 | | 6/1963 | Saperstein | 128/355 |
| 3,861,870 | * | 1/1975 | Edwards | 8/115.6 |
| 4,048,123 | | 9/1977 | Hramchenko | 252/545 |
| 4,352,678 | * | 10/1982 | Jones | 51/30 D |
| 4,457,856 | * | 7/1984 | Mitchell | 252/166 |
| 4,508,634 | | 4/1985 | Elepano . | |
| 4,537,604 | * | 8/1985 | Dawson | 51/298 |
| 4,614,606 | * | 9/1986 | Machin | 252/116 |
| 4,673,526 | * | 6/1987 | Zabolto | 252/174.16 |
| 4,704,222 | * | 11/1987 | Smith | 252/106 |
| 4,788,005 | * | 11/1988 | Castro | 252/539 |
| 4,911,857 | * | 3/1990 | Machin | 252/98 |

FOREIGN PATENT DOCUMENTS

| 050887 | 5/1982 | (EP) . |
| 179264 | 4/1986 | (EP) . |
| 257458 | 3/1988 | (EP) . |
| 295886 | 12/1988 | (EP) . |
| 2595249 | 3/1986 | (FR) . |
| 2140451 | 11/1984 | (GB) . |
| 2181738 | 4/1987 | (GB) . |
| 56-131512 | 3/1980 | (JP) . |
| 60-152407 | 1/1984 | (JP) . |
| 60/006795 | 1/1985 | (JP) . |
| 60/108499 | 6/1985 | (JP) . |
| 62/212498 | 9/1987 | (JP) . |

OTHER PUBLICATIONS

"Cosmetics and Toiletries" vol. 101, Jul., 1986.
European Search Report & Annex.

* cited by examiner

*Primary Examiner*—Thurman K. Page
*Assistant Examiner*—Brian K. Seidleck
(74) *Attorney, Agent, or Firm*—Ronald A. Koatz

(57) ABSTRACT

A viscous, liquid, skin washing composition comprising water, at least one surface active agent, abrasive particles and a viscosifier, CHARACTERISED IN THAT the viscosity of the composition is typically that of a shower gel, i.e. in the range 4000–8000 mPas measured at a shear rate of 10 $s^{-1}$, the particles, preferably calcite, have a mean diameter of 40–400 micrometres and a bulk density of 1–4.

1 Claim, No Drawings

METHOD OF EXFOLIATING SKIN

CROSS-REFERENCES

The present application is filed as a Divisional application which is a Continuation of U.S. Ser. No. 08/417,702 filed Apr. 6, 1995, now abandoned, which in turn is a Continuation of U.S. Ser. No. 08/065,330 filed May 20, 1993, now abandoned.

TECHNICAL FIELD

The present invention relates to exfoliant compositions.

BACKGROUND TO THE INVENTION

The skin of the human body periodically requires deep cleansing in order to remove therefrom sebaceous secretions, soil deposits and dead skin resulting from desquamation of the epidermal tissue. Exfoliation can be accomplished by the use of a rough cleaning rag, a natural sponge or an exfoliant composition.

Known exfoliant compositions comprise an abrasive component to facilitate removal of the above-mentioned substances and debris. While such compositions are generally applied to the skin for cosmetic purposes, their use as paint removers (for use, for instance, after decorating) and in methods of medical treatment, such as treatment of acne, has also been proposed. It has been suggested that exfoliative cleaning promotes regeneration of the epidermal tissues such that the skin regains suppleness. It has also been proposed that the penetration of cosmetic or dermo-pharmaceutical products is facilitated by exfoliation.

Known exfoliant abrasives include hydrogenated fats, inorganic salts such as sodium citrate or relatively low-molecular weight organics, such as sugars (U.S. Pat. No. 4,048,123); synthetic polymers such as polyethylene powders and granulated particles (JP 60-152407) or organo-polysiloxane (EP 295886); vegetable matter such as the endocarp of apricot, peach and walnut seeds, almond flesh, and wood flour (U.S. Pat. No. 4,508,634). Traditionally, birch powder or coconut pulp have been suggested as exfoliants. Other proposals have related to the use of animal matter such as pearl dust (JP 56-131512) or powdered crab shell and finely ground minerals such as, silica or 10 micron glacial limestone of a highly specific type (EP 257458). A general review of scrub cosmetics can be found in 'Cosmetics and Toiletries', volume 101, July 1986.

Mineral exfoliants also include those listed in the patent of Saperstein (U.S. Pat. No. 3,092,111) wherein the use of aluminium oxide, synthetic alumina, corundum, volcanic ash, diatomaceous earth, bentonite, feldspar and silica is suggested. Known exfoliant compositions are provided as thick pastes for topical administration to small regions of the body such as the face or feet.

BRIEF DESCRIPTION OF THE INVENTION

We have now devised a viscous, liquid, skin washing composition comprising water, at least one surface active agent, suspended, abrasive particles and a viscosifier, CHARACTERISED IN THAT the viscosity of the composition is in the range 4000–8000 mpa.s measured at a shear rate of 10 s$^{-1}$ the particles have a mean diameter of 40–400 microns and the particles have a specific gravity in the range 1–4.

The above-mentioned, characteristic viscosity measurements may be determined exactly (as in the case of the non-zero shear viscosities) or may be obtained from an extrapolation according to the Cross model (as in the case of the zero shear viscosity).

In the specification, measurements of viscosity were made at 25° C. using a Haake RV20 Rotoviscometer using ether an SV1 or an NV cup and bob.

In general, the compositions will exhibit an extrapolated Newtonian viscosity at a low shear rate of at least 10,000 Pa.s, preferably greater than 40,000 Pa.s, most preferably greater than 100,000 Pas.

DETAILED DESCRIPTION OF THE INVENTION

Abrasive

The presence of abrasive particles have a mean diameter of 40–400 microns and a specific gravity in the range 1–4 is an essential element of the present invention.

We have determined that water-insoluble mineral particles are particularly well-suited for use in exfoliant compositions according to the present invention.

In particular, minerals are free of bacterial and/or fungal contamination and have a reduced tendency to generate immunochemical responses at the skin surface. It is known that materials which are potentially contaminated with bacteria and other pathogens can be sterilised by the use of gamma radiation but this pretreatment of raw materials is expensive and has been found to be unacceptable to some groups of consumers.

Preferred minerals have a Moh hardness of 1–6 so as to avoid excessive abrasion of and damage to the skin.

Particularly preferred minerals have a Moh hardness in the range 2.5–4.0.

Calcite (3 Moh) particles are most particularly preferred.

Calcite particles of a size range of 50–400 microns and a mean particle size of 130 microns are available as 'DURCAL 130' [RTM] from Croxton & Garry. Preferred products comprise 5–15% wt. of mineral particles, more preferably around 10% wt.

Preferred particle sizes are such that the bulk of the particles have a mean size in the range 40–250 microns. The preferred particle size distribution is such that 80–95% wt of the particles have a mean size of less than 250 microns, 55–75% wt of the particles have a mean size of less than 150 microns and less than 10% wt have a mean size of less than 10 microns, i.e over 50% wt of the particles have a mean size in the range 40–250 microns.

The relatively large size of the particles is important in establishing the correct 'in-use feel' of the products.

As is shown below by way of example, when smaller particles are used the products did not score as well in comparative human studies.

Viscosity Modifiers

A viscosity in the range 4000–8000 mPas measured at a shear rate of 10 s$^{-1}$, is an essential element of the present invention.

Whereas known exfoliant compositions have viscosities very much higher than that of embodiments of the present invention, the embodiments of the present invention have viscosities which are similar to 'shower-gel' compositions.

Shower-gels themselves typically have a viscosity which is higher than that of other liquid washing products such some facial cleaners and shampoo compositions. This relatively high viscosity of shower gel compositions is normally achieved by the formation of rod-micelles which do not suspend particles. For example a typical embodiment of the present invention has a viscosity a 1 Hz shear of around 12320 mPa.s. The viscosity of a hair shampoo (TIMOTEI [RTM]) measured under the same conditions is lower, around 3587 mPa.s and would not support calcite. Similarly, at 10 Hz, the viscosity of a typical embodiment of the invention is 4800 mPa.s whereas the shampoo composition has a viscosity of 3164 mPa.s. For pasty compositions, such as DOVE [RTM] facial wash, the viscosities at 1 and 10 Hz are 84360 mPa.s and 11980 mPa.s respectively, much higher than the composition of the invention.

It will be noted from the above-mentioned figures that the embodiments of the present invention generally have a ratio of viscosity at 1 Hz:10 Hz between 2 and 5, i.e. shear thinning occurs over this range.

Compositions according to the present invention comprise a viscosifier, preferably a swelling clay, more preferably a synthetic hectorite (laponite) clay.

In a particularly preferred embodiment of the invention the composition comprises a hectorite clay and further comprises an electrolyte salt capable of causing the clay to thicken so as to suspend the exfoliant particles.

Preferred levels of clay range from 1–2% wt, with an electrolyte level of 0.1–2.0%, 1.0–2.0% being preferred.

Suitable electrolytes include alkaline and alkaline earth salts such as halides, ammonium salts and sulphates.

It should be noted that, with commercial hectorites, some minor experimentation is required to determine the exact level of electrolyte needed to reach a particular viscosity: this arises from variations in the properties of hectorite as received and from variations in either the level of or the electrolyte content of surfactant raw materials.

As an alternative a thickening polymer can be employed, either alone or in combination with other viscosifiers such as swelling clays. Preferred polymers are the natural gums including alginates, guar, xanthan and polysaccharide derivatives including carboxy methyl cellulose and hydroxypropyl guar. Xanthan gums are particularly preferred. Xanthan gums have the advantageous feature of shear thinning, while the high viscosity is recovered upon reduction of stress. This facilitates the suspension of particles of the size and specific gravity necessary for the present invention. Combinations of xanthan gums and hectorites have been found to be particularly useful.

Surfactant

The presence of at least one surface active agent is an essential element of the present invention.

The surfactant can be selected from any known surfactant suitable for topical application to the human body. Mild surfactants are particularly preferred as is the presence of co-surfactants with skin-mildness benefits.

Preferred levels of surfactant range from 10–30% wt, preferably comprising 5–20% wt of anionic surfactant. Suitable anionic surfactants are selected from alkyl ether sulphates, acyl isethionates, alkyl sulphosuccinates, alkyl amido sulphosuccinates, alkyl glyceryl ether sulphonates, methyl acyl taurates, alkyl phosphate esters, acyl sarcosinates and mixtures thereof. The preferred anionic surfactant being an alkyl ether sulphate.

It is also preferable that the composition comprises 5–10% wt of a co-surfactant. Suitable co-surfactants can be selected from the group comprising betaines, amido-propyl betaines, amidopropyl sultaines and mixtures thereof. The co-surfactant is most preferably a betaine.

Compositions according to the present invention can further comprise one or more of a nonionic surfactant such as an alkyl polysaccharide, lactobionamide or alcohol ethoxylate.

Minors

Other inessential but typical components of the compositions according to the present invention can be selected from one or more of opacifiers, preferably 0.2–2.0% wt; preservatives, preferably 0.2–2.0% wt and perfumes, preferably 0.5–2.0 wt%. Optional components include colouring agents, germicides, conditioning agents, emollients, humectants, moisturisers, anti-oxidants and preservatives.

In order that the present invention may be better. understood it will be further described hereafter with reference to examples of embodiments of the invention.

EXAMPLES

An exfoliant composition was preferred with the following composition (all quantities being given in wt% or wt parts on product as mentioned):

| COMPOSITION 1: | |
|---|---|
| sodium lauryl ether (3EO) sulphate: | 11.70% |
| sodium coco amido propyl betaine: | 1.80% |
| calcite (DURCAL 130: RTM ex Croxton & Garry): | 10.00% |
| perfume: | 1.00% |
| hectorite (LAPONITE XLS: RTM ex Laporte): | 1.35% |
| NaCl: | 0.45% |
| preservative: | 0.63% |
| opacifier: | 0.40% |
| water: | to 100% |

Stock solution of 7.5% wt Hectorite sol was prepared by vigorously mixing 925 parts of water with 75 parts of slowly added Laponite XLS (ex. Laporte) at 40 Centigrade. Agitation was maintained for an hour to ensure complete dispersion and hydration of clay and to allow the sol to cool to near ambient temperature. Homogeneity of a sample of the sol can be ensured by observing a sample under an optical microscope. and continuing mixing if full hydration has not occurred.

Stock solution of sodium lauryl ether (3EO) sulphate (SLES, ex. Hoechst) at a concentration of (25% AD) was prepared using a high shear mixer.

The SLES solution, opacifier and preservatives were combined in a mixing vessel capable of operating under vacuum and fitted with a high and low shear mixer and recirculation loop. The mix was recirculated under vacuum and the hectorite sol drawn into the vessel via the high shear mixer, followed by the perfume and the betaine (30% AD).

With the recirculation stopped, part of the salt, as a 25% solution was added to the mix under vacuum. The calcite powder was drawn into the vessel under vacuum and gradually incorporated into the product at low shear.

Small samples of the product were removed and mixed with a range of salt solutions in order to determine the quantity of salt required to achieve the desired viscosity. The required quantity of salt was added in solution in the final 60 parts of water.

The Ph of the product thus obtained was measured as 8.09 and the viscosity was determined to be 6100 Mpas $10s^{-1}$ by the method given above.

The above-mentioned example was repeated with a finer grade calcite material available in the marketplace as Durcal 40 [RTM] ex Croxton and Garry.

Comparative size data for these materials are given below in Table 1 (manufacturers data).

The data given include the 'cut-off' in microns below which the proportion of particles was assessed (i.e. Durcal-130 comprises 55–75% wt of particles with a mean diameter of less than 150 microns).

TABLE 1

| Cut-off | (A) Durcal-130 | (B) Durcal-40 |
|---|---|---|
| 250 | 80–95% | — |
| 200 | — | 99–5% |
| 150 | 55–75% | — |
| 100 | 20–30% | 90% |
| 75 | — | 81% |
| 50 | — | 65% |
| 40 | >10% | — |
| 20 | — | 35% |
| 10 | — | 10% |

Sensory evaluation of compositions (A) and (B) by trained panellists indicated that (A) was significantly grittier than (B) as expected. Composition (A) also gave a significantly smoother skin feel in post-washing assessment of human skin, using standard test techniques as follows:

40 panellists were pre-wetted with tap-water at a temperature of 32–34° C. on both forearm and elbow. Test products were dispensed ad libitum by the panellists onto the hand and the wetted area was washed with the product, rinsed with tap water and dries with a paper towel. Panellists were then asked to state the extent to which an attribute was present in products. Results were analysed using a two way analysis of variance and attribute differences considered significant at a better than 95% confidence interval.

Significant differences favouring the coarser Durcal 130 (composition A) were noted for the descriptors 'rejuvenates skin' and 'cleans skin thoroughly' with a 1% chance of the results being an artifact. With a 0.1% chance of an artifact differences noted were equated with the statements: 'gently removes dead cells', skin feels fresh/healthy and 'skin feels smooth/supple'.

Further samples of the product were prepared with the following formulation:

| COMPOSITION 2: | |
|---|---|
| sodium lauryl ether (3EO) sulphate: | 11.70% |
| sodium coco amido propyl betaine: | 1.80% |
| calcite (DURCAL 130: RTM ex Croxton & Garry): | 10.00% |
| perfume: | 1.00% |
| hectorite (LAPONITE XLS: RTM ex Laporte): | 1.35% |
| xanthan gum (KELZAN S: RTM ex Kelco): | 0.20% |
| NaCl: | see below |
| preservative: | 0.63% |
| opacifier: | 0.40% |
| water: | to 100% |

The salt level for the composition 2 was varied as shown in Table 2 below, and products obtained with the properties given in the table.

TABLE 2

| | Visc. Pa · s | | stability | |
|---|---|---|---|---|
| % Salt | 10 Hz | zero | ambient | 37 C. |
| 1.10 | 3.7 | 33000 | 8 weeks | 2 weeks |
| 1.30 | 5.0 | 141000 | 12 weeks | 12 weeks |
| 1.50 | 6.6 | — | 12 weeks | 12 weeks |
| 1.77 | 9.1 | — | 12 weeks | 12 weeks |

From these results it can be seen that adequately stable products could be prepared.

What is claimed is:

1. A method of exfoliating skin, wherein said method comprises:
   (a) applying to said skin a liquid composition comprising
      (i) water;
      (ii) 5 to 20 wt. % of an anionic surfactant selected from the group consisting of alkyl ether sulfates, acyl isethionates, alkyl sulfosuccinates, alkyl amido sulfosuccinates, alkyl glyceryl ether sulphonates, methyl acyl taurates, alkyl phosphate esters, acyl sarcosinates, and mixtures thereof;
      (iii) a cosurfactant selected from the group consisting of betaines, amidopropyl betaines, amidopropyl sultaines and mixtures thereof;
      (iv) abrasive particles having a mean diameter of 40 to 400 micrometers and a bulk density of 1 to 4; and
      (v) a viscosifer;
      wherein the composition has a viscosity in the range 4000–8000 mPas measured at a shear rate of 10 s$^{-1}$;
   wherein said composition is in rod micellar phase: and
   wherein ratio of viscosity at 1 Hz:10 Hz is between 2 and 5;
   (b) washing the skin with the composition; and
   (c) rinsing the composition off the skin.

* * * * *